United States Patent
Swedberg et al.

(10) Patent No.: US 10,993,857 B2
(45) Date of Patent: May 4, 2021

(54) ABSORBENT ARTICLE AND METHOD OF MANUFACTURING SAME

(71) Applicant: Essity Hygiene and Health Aktiebolag, Gothenburg (SE)

(72) Inventors: Maria Swedberg, Kungsbacka (SE); Anders Silfverstrand, Gothenburg (SE)

(73) Assignee: ESSITY HYGIENE AND HEALTH AKTIEBOOLAG, Gothenburg (SE)

( * ) Notice: Subject to any disclaimer, the term of this patent is extended or adjusted under 35 U.S.C. 154(b) by 0 days.

(21) Appl. No.: 16/955,895

(22) PCT Filed: Dec. 22, 2017

(86) PCT No.: PCT/EP2017/084479
§ 371 (c)(1),
(2) Date: Jun. 19, 2020

(87) PCT Pub. No.: WO2019/120576
PCT Pub. Date: Jun. 27, 2019

(65) Prior Publication Data
US 2020/0390618 A1 Dec. 17, 2020

(51) Int. Cl.
*A61F 13/56* (2006.01)
*A61F 13/62* (2006.01)
(Continued)

(52) U.S. Cl.
CPC .... *A61F 13/5622* (2013.01); *A61F 13/15203* (2013.01); *A61F 13/5512* (2013.01);
(Continued)

(58) Field of Classification Search
CPC ........... A61F 13/15765; A61F 13/5512; A61F 13/5622; A61F 13/62; A61F 13/625;
(Continued)

(56) References Cited

U.S. PATENT DOCUMENTS

| 5,413,568 A | 5/1995 | Roach et al. |
| 5,531,732 A * | 7/1996 | Wood .................... A61F 13/493 |
| | | 604/391 |

(Continued)

FOREIGN PATENT DOCUMENTS

| CN | 1296401 A | 5/2001 |
| CN | 101346118 A | 1/2009 |

(Continued)

OTHER PUBLICATIONS

Office Action (Decision to Grant a Patent) dated Jul. 22, 2020, by the Japanese Patent Office in corresponding Japanese Patent Application No. 2019-500234, and an English Translation of the Office Action. (5 pages).

(Continued)

*Primary Examiner* — Catharine L Anderson
(74) *Attorney, Agent, or Firm* — Buchanan Ingersoll & Rooney P.C.

(57) ABSTRACT

An absorbent article comprises a layered structure with an absorbent material sandwiched between at least two layers of the structure, and at least one elongate tab. Each elongate tab comprises an attached portion by which the tab is attached to a first layer of the layered structure and a fastening portion provided for releasably engaging a landing zone on the absorbent article. Each tab is made of a predetermined material which is deformable by an energy source. The attached portion comprises a plurality of surface protrusions integrally formed of said material, each of said surface protrusions comprising a base portion and a head portion above the base portion. The attached portion is attached to said layer by deformed head portions of at least some of said surface protrusions. In a method for manufacturing such article, the attachment involves deforming head portions of the surface protrusions.

24 Claims, 7 Drawing Sheets

(51) Int. Cl.
*A61F 13/15* (2006.01)
*A61F 13/551* (2006.01)

(52) U.S. Cl.
CPC .. *A61F 13/625* (2013.01); *A61F 2013/15406* (2013.01); *A61F 2013/15869* (2013.01); *A61F 2013/15878* (2013.01); *A61F 2013/15894* (2013.01)

(58) Field of Classification Search
CPC .. A61F 2013/15869; A61F 2013/15878; A61F 2013/15894; A61F 2013/5666; A61F 2013/8402
See application file for complete search history.

(56) References Cited

U.S. PATENT DOCUMENTS

| | | | |
|---|---|---|---|
| 5,785,699 | A | 7/1998 | Schmitz |
| 6,007,527 | A * | 12/1999 | Kawaguchi ......... A61F 13/5512 156/315 |
| 6,036,679 | A | 3/2000 | Balzar et al. |
| 6,287,665 | B1 | 9/2001 | Hammer |
| 6,746,434 | B2 | 6/2004 | Johnson et al. |
| 7,018,496 | B1 | 3/2006 | George et al. |
| 7,857,801 | B2 | 12/2010 | Hamall et al. |
| 8,197,458 | B2 | 6/2012 | Baeck |
| 8,298,205 | B2 | 10/2012 | Norrby et al. |
| 8,585,672 | B2 | 11/2013 | Lavon et al. |
| 8,663,184 | B2 | 3/2014 | Liu et al. |
| 8,784,722 | B2 | 7/2014 | Rocha |
| 9,834,355 | B2 | 12/2017 | Dahlqvist et al. |
| 10,076,162 | B2 | 9/2018 | Rocha |
| 2002/0023321 | A1 | 2/2002 | Clune |
| 2003/0120253 | A1 * | 6/2003 | Wentzel ................ A61F 13/64 604/392 |
| 2008/0038507 | A1 | 2/2008 | Seth et al. |
| 2010/0180407 | A1 | 7/2010 | Rocha |
| 2017/0087034 | A1 | 3/2017 | Bosser |
| 2019/0016058 | A1 | 1/2019 | Tuma |
| 2019/0224054 | A1 | 7/2019 | Silfverstrand et al. |

FOREIGN PATENT DOCUMENTS

| | | |
|---|---|---|
| CN | 101500521 A | 8/2009 |
| CN | 101534778 A | 9/2009 |
| CN | 101641066 A | 2/2010 |
| CN | 102341228 A | 2/2012 |
| CN | 106170276 A | 11/2016 |
| DE | 10102501 A1 | 8/2002 |
| DE | 102016000756 A1 | 7/2017 |
| EP | 1529506 A1 | 5/2005 |
| EP | 2926787 A1 | 10/2015 |
| JP | H10511868 A | 11/1998 |
| JP | 2000-000269 A | 1/2000 |
| JP | 2003-535649 A | 12/2003 |
| JP | 2014104147 A | 6/2014 |
| RU | 2395265 C1 | 7/2010 |
| RU | 2396932 C1 | 8/2010 |
| RU | 2400199 C2 | 9/2010 |
| RU | 2404057 C2 | 11/2010 |
| TW | 201545729 A | 12/2015 |
| WO | 95/30397 A1 | 11/1995 |
| WO | 96/20675 A1 | 7/1996 |
| WO | 99/53881 A1 | 10/1999 |
| WO | 00/27236 A1 | 5/2000 |
| WO | 0197738 A2 | 12/2001 |
| WO | 0226182 A2 | 4/2002 |
| WO | 2008060204 A1 | 5/2008 |
| WO | 2009136826 A1 | 11/2009 |
| WO | 2010085492 A1 | 7/2010 |
| WO | 2013162430 A1 | 10/2013 |
| WO | 2015190964 A1 | 12/2015 |
| WO | 2015190966 A1 | 12/2015 |
| WO | 2016/081438 A1 | 5/2016 |
| WO | 2016/149243 A1 | 9/2016 |

OTHER PUBLICATIONS

Chinese Office Action for Chinese Application No. 201680087410. 1, dated May 15, 2020, with translation, 26 pages.
European Office Action for European Application No. 16734682.4, dated Jun. 19, 2019, 3 pages.
International Preliminary Report on Patentability for Application No. PCT/EP2016/065862, dated Jul. 11, 2018, 6 pages.
Non-Final Office Action issued by the U.S. Patent and Trademark Office in U.S. Appl. No. 16/314,234 dated Oct. 8, 2020, U.S. Patent and Trademark Office, Alexandria, VA. (10 pages).
Decision to Grant dated Oct. 26, 2020, by the Federal Service for Intellectual Property in corresponding Russian Patent Application No. 2020124162 and an English translation of the Decision. (21 pages).
Office Action (Notification of the First Office Action) dated Dec. 4, 2020 by the China National Intellectual Property Administration (CNIPA) of the People's Republic of China in corresponding Chinese Patent Application No. 201780097815.8, and an English Translation of the Office Action. (23 pages).
Notice of Allowance dated Dec. 21, 2020, by the U.S. Patent and Trademark Office in U.S. Appl. No. 16/956,238. (10 pages).
Notification of the First Office Action dated Dec. 16, 2020, by the National Intellectual Property Administration (CNIPA) of the People's Republic of China in Chinese Patent Application No. 201780097814.3 and an English translation of the Office Action. (23 pages).
Brazil Office Action for Brazil Application No. BR112018076381-0, dated May 18, 2020, 4 pages.
Chinese Office Action for Chinese Application No. 201680087410. 1, dated Jan. 19, 2020, with translation, 17 pages.
Chinese Office Action for Chinese Application No. 201680087410. 1, dated Jul. 15, 2019, with translation—22 pages.
Chinese Office Action for Chinese Application No. 201680087419. 2, dated Jun. 28, 2019, with translation, 16 pages.
International Preliminary Report on Patentability (PCT/IPEA/409) dated Jul. 18, 2018, by the European Patent Office as the International Preliminary Examining Authority for International Application No. PCT/EP2016/065851.
International Preliminary Report on Patentability (PCT/IPEA/409) dated Feb. 27, 2020, by the European Patent Office as the International Preliminary Examining Authority for International Application No. PCT/EP2017/084476.
International Preliminary Report on Patentability (PCT/IPEA/409) dated Mar. 30, 2020, by the European Patent Office as the International Preliminary Examining Authority for International Application No. PCT/EP2017/084479.
International Search Report (PCT/ISA/210) and Written Opinion (PCT/ISA/237) dated Feb. 15, 2017, by the European Patent Office as the International Searching Authority for International Application No. PCT/EP2016/065851.
International Search Report (PCT/ISA/210) and Written Opinion (PCT/ISA/237) dated Jul. 11, 2018, by the European Patent Office as the International Searching Authority for International Application No. PCT/EP2016/065862.
International Search Report (PCT/ISA/210) and Written Opinion (PCT/ISA/237) dated Jun. 27, 2018, by the European Patent Office as the International Searching Authority for International Application No. PCT/EP2017/084479.
International Search Report (PCT/ISA/210) dated Feb. 21, 2018, by the European Patent Office as the International Searching Authority for International Application No. PCT/EP2017/084476.
International Search Report and Written Opinion for Application No. PCT/EP2016/065862, dated Feb. 16, 2017—10 pages.
Notice of Reasons for Rejection for Japanese Application No. 2019-500234, dated Dec. 16, 2019, with translation, 5 pages.
Russian Decision to Grant a Patent for Russian Application No. 2019101795, dated May 24, 2019, with translation, 13 pages.
Written Opinion (PCT/IPEA/408) dated Nov. 15, 2019, by the European Patent Office as the International Preliminary Examining Authority for International Application No. PCT/EP2017/084479.

(56) References Cited

OTHER PUBLICATIONS

Written Opinion (PCT/ISA/237) dated Feb. 21, 2018, by the European Patent Office as the International Searching Authority for International Application No. PCT/EP2017/084476.

* cited by examiner

ABSORBENT ARTICLE AND METHOD OF MANUFACTURING SAME

FIELD OF THE DISCLOSURE

The present disclosure relates to an absorbent article and a method of manufacturing said absorbent article

BACKGROUND ART

Known absorbent articles, such as diapers, comprise a layered structure enclosing an absorbent material and at least one elongate tab, such as for example lateral fastening tabs for laterally fastening side panels of the article to each other or a disposal tab which is wrapped around the article when it is thrown away. Such tabs are commonly attached to the layered structure by means of an adhesive and have a fastening portion with hooks provided for releasably engaging a landing zone on another part of the absorbent article.

From U.S. Pat. No. 6,746,434 B2 an absorbent article is known which comprises a garment material of which part of its surface is mechanically modified to form a plurality of surface protrusions integrally from the garment material. The absorbent article further comprises a landing zone having a plurality of fibrous loops adapted to engage with the surface protrusions to provide a fastening mechanism. U.S. Pat. No. 6,746,434 B2 further describes a method for mechanically forming the surface protrusions on the garment material.

A method for forming such surface protrusions on a substrate is further known from WO 2010/085492 A1.

SUMMARY

It is a first aim of the present disclosure to provide an absorbent article of the type comprising a layered structure with an absorbent material sandwiched between at least two layers and at least one elongate tab attached to at least one layer of the layered structure, wherein the tab is more strongly attached to the layer, preferably without the use of adhesive.

It is a second aim of the present disclosure to provide a method of manufacturing such an absorbent article, whereby a stronger attachment of the tab to the layer can be achieved, preferably without the use of adhesive.

The disclosure provides, according to a first aspect, an absorbent article comprising a layered structure with an absorbent material sandwiched between at least two layers of said layered structure, such as for example a diaper, and at least one elongate tab. Each elongate tab comprising an attached portion by which the tab is attached to at least one layer of the layered structure and a fastening portion provided for releasably engaging a landing zone on the absorbent article. At least the attached portion of each tab is made of a predetermined material which is deformable by means of an energy source. The attached portion comprises a plurality of surface protrusions which are integrally formed of said material, each of said surface protrusions comprising a base portion and a head portion above the base portion. The attached portion is attached to said layer by means of deformed head portions of at least some of said surface protrusions.

It has been found that in this way a strong attachment with a mechanical bond may be achieved, e.g., a firm releasable attachment which may be stronger than a typical hook-and-loop fastener, or alternatively a permanent attachment (which cannot be released without damaging the article), and that the use of adhesive for attaching the elongate tab to the layer can be avoided. The use of adhesive can be undesirable because it may be hard to control the amount of adhesive that comes out of an adhesive applicator and the adhesive may contaminate the production line. The use of adhesive can be further undesirable because it may be transferred to the wearer's clothes.

In embodiments according to the disclosure, the tab may be permanently attached to at least one layer of the layered structure. Permanently attached means that it cannot be released without damaging the article. Depending on the material and structure of the at least one layer of the layered structure and the head portions, some of the head portions may be heat-bonded to or fused with the layered structure.

The present disclosure is of particular advantage for attaching a disposal tab to the backsheet of a baby diaper: in this field it is nowadays common to treat the fibres of the backsheet with substances, e.g., by adding low molecular weight waxes to soften the material, which may decrease adhesion of adhesives commonly used to attach the disposal tab. The present disclosure provides a solution in which the use of adhesive may no longer be required.

In embodiments according to the disclosure, the deformed head portions may take the form of rivets or in general be wider than the base portions, such that fibres of said layer may be engaged by the surface protrusions of the attached portion. Depending on the material and structure of the at least one layer of the layered structure, in particular the melting temperatures, some of the head portions may be bonded to or fused with the material(s) of the at least one layer. Depending on manufacturing process parameters, e.g., time and heat exposure, at least some of the base portions of the surface protrusions of the attached portion may also be at least partly deformed.

In embodiments according to the disclosure, the predetermined material of the attached portion and a thermoplastic material of the layer to which the tab is attached may have different melting temperatures, the predetermined material preferably having a lower melting temperature.

In embodiments according to the disclosure, the predetermined material of the attached portion and a material of the layer to which the tab is attached may be incompatible polymer blends, also known as immiscible or heterogeneous.

In embodiments according to the disclosure, the predetermined material of the attached portion and a material of the layer to which the tab is attached may be compatible polymer blends.

In embodiments according to the disclosure, the absorbent material sandwiched between at least two layers of said layered structure may be an absorbent core. The layered structure may comprise a liquid-permeable topsheet and a liquid-impermeable backsheet. The absorbent core may be arranged along a longitudinal axis of the layered structure and a transversal axis extending in a perpendicular direction in relation to the longitudinal axis, and said article may define a front portion, a back portion and a crotch portion.

In embodiments according to the disclosure, the fastening portion may comprise hooks which are integrally formed of the same material as the surface protrusions of the attached portion. These hooks may attach to a part of the layered structure, e.g., a predetermined landing zone, like a common hook and loop structure. The construction in the same material has the advantage of enabling an economical manufacturing process, in which for example the hooks and the surface protrusions may be formed in the same step. In embodiments, the surface protrusions which are initially formed for the attached portion may also take the form of hooks, head portions of which are further deformed for the attachment. This has the advantage that the hooks can already engage said layer before the further deformation step and thus ensure that the position of the tab on the layer is maintained until the further deformation step.

In embodiments according to the disclosure, the at least one elongate tab may comprise a complete layer of said material or may be fully made of said material. Said material is preferably a thermoplastic material. The at least one elongate tab is preferably a film, a (nonwoven) web, a sheet, or a laminate, for example a film and a nonwoven laminated together.

In embodiments according to the disclosure, the material may be a thermoplastic material deformable by means of an energy source chosen from: heat, ultrasonic vibrations, micro waves, infrared radiation.

In embodiments according to the disclosure, the at least one elongate tab may comprise a disposal tab attached to an outer layer of the layered structure and provided for being wrapped around the absorbent article. After use, absorbent articles are usually folded or rolled up so that the soiled portion is wrapped inside for disposal. In order to prevent the soiled article unfolding and to keep the soiled portion inside, it is desired that a so-called disposal tab is arranged to keep the article in the folded or rolled-up state under disposal.

In embodiments according to the disclosure, the disposal tab may be a Z-folded tab, a bottom layer of the Z-folded tab comprising the attached portion which is attached to the outer layer of the layered structure and a top layer of the Z-folded tab comprising the fastening portion, preferably with integrally formed hooks, for releasably engaging a first zone on the outer layer of the layered structure while the tab is folded and a second zone on the outer layer of the layered structure when the tab is wrapped around the article. The layers of the Z-folded tab may be adherent to each other, for example by means of adhesive between the bottom and middle layers and between the middle and top layers, or as a result of the material of the layers being self-adherent.

In embodiments according to the disclosure, the at least one elongate tab may be stretchable or elastic. For example, the disposal tab may be stretchable or elastic to an extent that it is capable of being wrapped around the absorbent article.

In embodiments according to the disclosure, the at least one elongate tab may be a fastening tab attached to a first side portion of the layered structure and provided for being fastened to one or more landing zones on a surface of the layered structure, for example on second side portions of the layered structure, for example to fasten the absorbent article around a wearer's waist.

In embodiments according to the disclosure, the first side portions may be side panels of the layered structure at a rear body portion of the article. The first side panels may be made of a nonwoven material. The fastening tabs may be each attached to a first surface of the respective side panel and folded such that the fastening portion releasably engages a zone on the first surface of the side panel or a zone on a second surface of the side panel opposite the first surface.

In embodiments according to the disclosure, the second side portions may be side panels of the layered structure at a front body portion of the article. The second side panels may be made of a nonwoven material to provide the landing zones for the fastening portions of the fastening tabs.

In a second aspect, which may be combined with the other aspects and embodiments described herein, the disclosure provides a method of manufacturing an absorbent article with an absorbent material sandwiched between at least two layers of a layered structure, the method comprising the steps of: (a) providing a layer of said layered structure and at least one elongate tab, wherein at least a first portion of each tab is made of a predetermined material which is deformable by means of an energy source; (b) forming surface protrusions on at least said first portion of each tab by deforming said predetermined material by means of said energy source; (c) positioning each of said at least one elongate tab with respect to said layer, such that the first portion of the tab overlaps with the respective layer; and (d) attaching the first portion of each of said at least one elongate tab to the said layer by further deforming head portions of at least some of said surface protrusions of the first portion by means of said energy source, thereby creating an attached portion wherein the tab is attached to said layer by means of said deformed head portions.

It has been found that a strong, mechanical bond of the tab to the layer of the layered structure can be obtained by forming, in a first step (step b), surface protrusions on the first portion of the tab by deformation of the material by means of said energy source and in a second step (step d) attaching the tab to the layer by further deforming the head portions of at least some of the surface protrusions of the first portion by means of said energy source.

In embodiments according to the disclosure, a second portion of each tab may also be made of said material and surface protrusions may also be formed on said second portion in step b, thereby creating in said second portion a fastening portion provided for releasably engaging a landing zone on the absorbent article. In this way, a fastening portion may be obtained in the same step as the first deformation of the material of the first portion (the later attached portion of the tab). Possibly also further portions of the tab may be made of said material and deformed simultaneously with the first portions and/or the second portion, for example to form further fastening portions on the tab.

In embodiments according to the disclosure, the at least one elongate tab may comprise a complete layer of said predetermined material or may be fully made of said material.

In embodiments according to the disclosure, said material may be a thermoplastic material and the energy source may be chosen from: heat, ultrasonic vibrations, micro waves, infrared radiation.

In embodiments according to the disclosure, the method may further comprise the step of folding said at least one elongate tab.

BRIEF DESCRIPTION OF THE DRAWINGS

The present disclosure will be discussed in more detail below, with reference to the attached drawings.

DESCRIPTION OF EMBODIMENTS

The present disclosure will be described with respect to particular embodiments and with reference to certain drawings but the disclosure is not limited thereto. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the disclosure.

Furthermore, the terms first, second, third and the like in the description and in the claims, are used for distinguishing between similar elements and not necessarily for describing a sequential or chronological order. The terms are interchangeable under appropriate circumstances and the embodiments of the disclosure can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the disclosure described herein can operate in other orientations than described or illustrated herein.

Furthermore, the various embodiments, although referred to as "preferred" are to be construed as exemplary manners in which the disclosure may be implemented rather than as limiting the scope of the disclosure.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present disclosure, the only enumerated components of the device are A and B, and further the claim should be interpreted as including equivalents of those components.

As used herein, with "hooks" is intended to mean the hook parts or surface protrusions of a hook-and-loop type fastener which are adapted to be fastened to a zone comprising fibrous loops, referred to as the landing zone. The hooks can have any shape. Preferred examples of hooks comprise pins, for example straight pins, angled pins, curved pins, tapered pins, limbed or multi-limbed pins, hooks, limbed or multi-limbed hooks, mushroom shaped protrusions, palm tree shaped protrusions. The hooks may have any type of cross-section such as round, oval, square, rectangular, polygonal. The hooks preferably have a solid core. Within one fastening portion all hooks may have the same shape. Alternatively, one fastening portion may comprise several different shapes of hooks.

For the landing zone, any type of zone that is able to engage and preferably able to releasably engage with the surface protrusions can be considered. A landing zone can be a zone attached to the absorbent article, for example one or more landing zones attached to one or more side panels of the absorbent article, or a larger patch in the front portion of the absorbent article. Examples comprise a loop patch or a nonwoven, woven or knitted patch attached to the absorbent article for example by gluing, melting or stitching. Alternatively, the material of part of the absorbent article can act as landing zone, e.g., part or the whole outer cover of the absorbent article, or the material of one or more side panels. For example if the outer cover or part thereof, or the side panels, comprises a nonwoven.

The fastening portions described herein can include any number of hooks, possibly arranged in arrays or zones within the fastening portion. Further, the fastening portions can have various densities. By the "density" is meant herein the number of hooks per area unit (square inch or square mm). The density of the fastening portion may affect flexibility and softness of hook-and-loop type fasteners. For example, a lower density area generally provides higher material flexibility and softness. However, in order to provide a certain holding force between the engaging hooks and loops, a certain number of hooks should preferably be available for engagement.

"Absorbent articles" according to the present disclosure may refer to consumer products of the type which absorb and contain body exudates, and more specifically, refers to products which are placed against or in proximity to the body of the wearer to absorb and contain the various exudates discharged from the body. Absorbent articles, comprise, for example, diapers and incontinence devices. Diapers comprise for example all-in-one diapers, pant diapers and belt diapers. The diapers can be diapers for babies, young children or adults. Absorbent articles comprise a layered structure with an absorbent material sandwiched between at least two layers of said layered structure. For example, the absorbent material may be part of an absorbent core sandwiched between the layers structure, which for example may be a liquid-permeable topsheet and a liquid-impermeable backsheet. The absorbent article may comprise a front portion, a back portion and a crotch portion extending between the front portion and the back portion. Preferably, the front portion and/or the back portion comprises a waist portion. The waist portion is preferably stretchable or elastic So-called all-in-one diapers are characterized in that they include fastening tabs with which the front and rear portion of the diaper are joined when the diaper is applied around the waist of a user. The fastening tabs may be attached to the layered structure with an absorbent material sandwiched between at least two layers of said layered structure.

So-called pant diapers are characterized in that the front and rear portion of the diaper are joined at the waist. This type of diaper is intended to be put on a user precisely like a pair of underpants, i.e., drawn over the user's legs and hips. The joining at the waist part of the pant diapers can usually be broken open to remove the pant diapers from the user so that is not necessarily required to pull the pants down over the user's legs and feet to remove the pant diaper. Pant diapers normally comprise both elastic areas in the waist section and around the leg openings. Pant diapers that can be opened and reclosed by means of refastening means also exist. Such pant diapers can be opened for example to check the contents of the article or to adjust the width of the article and then reclosed afterwards.

So-called belt diapers are characterized in that they comprise a belt that is transverse oriented in relation to the absorbent part of the diaper and which is attached integrally with the chassis, i.e., attached to the layered structure with the absorbent material sandwiched between at least two layers of said layered structure, or the absorbent part. The belt may have two belt portions extending on either side of the rear end or the front end of the chassis or the absorbent part. When putting on a belt diaper, the two belt portions are intended to be fastened around the waist of the wearer in a first stage. The front end or the rear end of the absorbent part of the belt diaper is hanging loose from the belt between the legs of the wearer. Once the belt portions have been joined together, the absorbent part is led between the user's legs and fastened to the belt, wherein the belt comprises fixing surfaces intended to stick to a fixing element arranged on the absorbent part of the diaper by its free transverse edge. Another type of belt diaper is in two pieces and comprises a separate belt and a separate absorbent structure. When in use the belt is fastened around the user's waist, following which the absorbent structure is joined to the outside of the belt by means of hook and loop elements or tape elements in the corners of the absorption structure.

The absorbent article according to the present disclosure can be a disposable article or a non-disposable article. The term "disposable" is used to describe absorbent articles which generally are not intended to be laundered or otherwise restored, or reused as an absorbent article, e.g., they are intended, to be discarded after a single use and may also be configured to be recycled, composted or otherwise disposed of in an environmentally compatible manner.

A disposal tab may be provided on the outside of a disposable article and intended for being wrapped around the article to enable the article to be disposed in a compact form with the absorbed fluids safely contained. The disposal tab generally has a part which is attached to the article and a part which is releasable and possibly stretchable or elastic for being wrapped around the article.

In embodiments according to the present disclosure, the absorbent part of the absorbent articles is generally formed by a layered structure containing a core of absorbent material. The core may be sandwiched by a topsheet and a backsheet. The topsheet is permeable to the fluid(s) to be absorbed; the backsheet is impermeable to these fluids. Additional layers may be provided between the topsheet or backsheet and the core to improve absorption and/or retention of the fluids. A core wrap of for example nonwoven may enclose the core.

Embodiments of absorbent articles are described herein which comprise "side panels", also attached to the layered structure. The side panels of the absorbent article may comprise, for example, a polymer film or foil, a coated film or foil, for example a polymer coated film or foil, a textile substrate such as a woven structure or a nonwoven substrate or a coated textile substrate, for example a polymer coated textile structure. The side panel preferably comprises a thermoplastic material. Examples of thermoplastic materials comprise polyamide, polyolefin such as polypropylene and polyethylene, polystyrene such as styrene-isoprene-styrene (SIS), styrene-butadiene-styrene (SBS), styrene-ethylene-butylene-styrene (SEBS), acrylonitrile-butadiene-styrene (ABS), polyester, polycarbonate, polyvinyl chloride (PVC), polyetherester, polyetheramine, PLA, polylactic acid (polyester), thermoplastic starch, cellulose esters, polyhydroxyalkanoates (PHAs) like the poly-3-hydroxybutyrate (PHB), polyhydroxyvalerate (PHV), polyhydroxyhexanoate (PHH), and blends thereof. The thermoplastic material may be modified or reinforced for example with fillers, fibers, flame retardants, colorants, etc. It is clear for a person skilled in the art that the side panel may comprise multiple layers for example a laminate comprising two or three layers.

Embodiments of absorbent articles are described herein which comprise portions made of predetermined materials which are deformable by means of an energy source. The energy source is used to deform these portions, at least partly, to form a weld for attachment of layers as well as to form hooks of a hook-and-loop type fastener. Preferred materials are thermoplastic materials, deformable by means of an energy source such as for example heat, ultrasonic vibrations, micro waves, infrared radiation or other. In this way, it is possible to form of the hooks and the weld simultaneously, i.e., in the same or substantially the same step in a production line. Examples of preferred thermoplastic materials comprise polyamide, polyolefin such as polypropylene and polyethylene, polystyrene such as styrene-isoprene-styrene (SIS), styrene-butadiene-styrene (SBS), styrene-ethylene-butylene-styrene (SEBS), acrylonitrile-butadiene-styrene (ABS), polyester, polycarbonate, polyvinyl chloride (PVC), polyetherester, polyetheramine, PLA, polylactic acid (polyester), thermoplastic starch, cellulose esters, polyhydroxyalkanoates (PHAs) like the poly-3-hydroxybutyrate (PHB), polyhydroxyvalerate (PHV), polyhydroxyhexanoate (PHH), and blends thereof. The thermoplastic material may be modified or reinforced for example with fillers, fibers, flame retardants, colorants, etc.

An embodiment of a sequence of process steps for attaching an elongate tab to a layer according to the present disclosure is described with reference to FIGS. 1-3.

Figure 1:
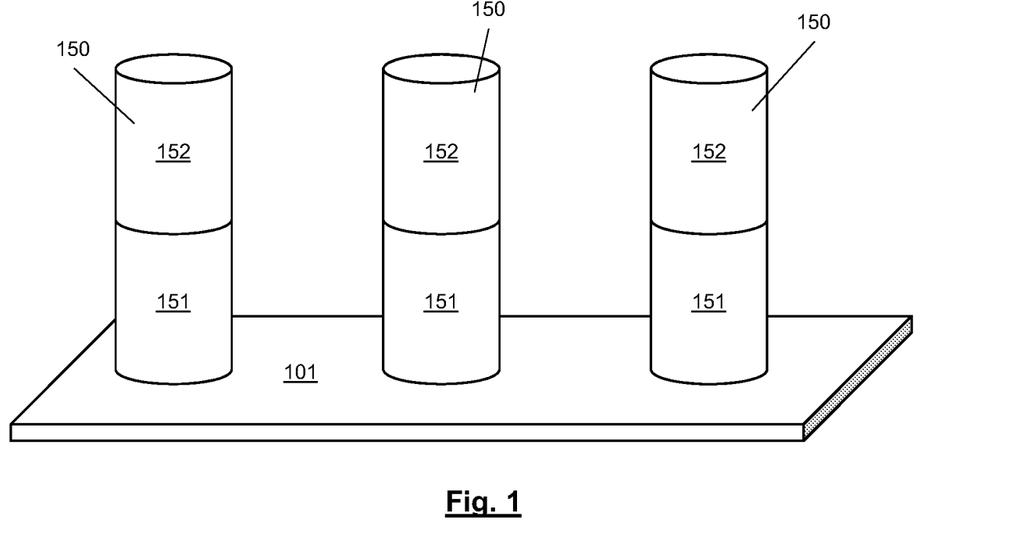
FIGS. 1-3 schematically show an exemplary embodiment of a sequence of process steps for attaching an elongate tab to a layer according to the present disclosure.

FIG. 1 schematically shows a detail of a portion of a layer 101 of an elongate tab 100. The portion of the layer 101 is made of the predetermined material and surface protrusions 150 are formed on this portion. The surface protrusions 150 comprise base portions 151 and head portions 152. In the embodiment shown the surface protrusions have a cylindrical shape, but a wide variety of other shapes are also possible, such as for example cuboid, bar-shaped, etc. The surface protrusions 150 may also have engaging shapes like the "hooks" of a hook-and-loop type fastener.

Figure 2:
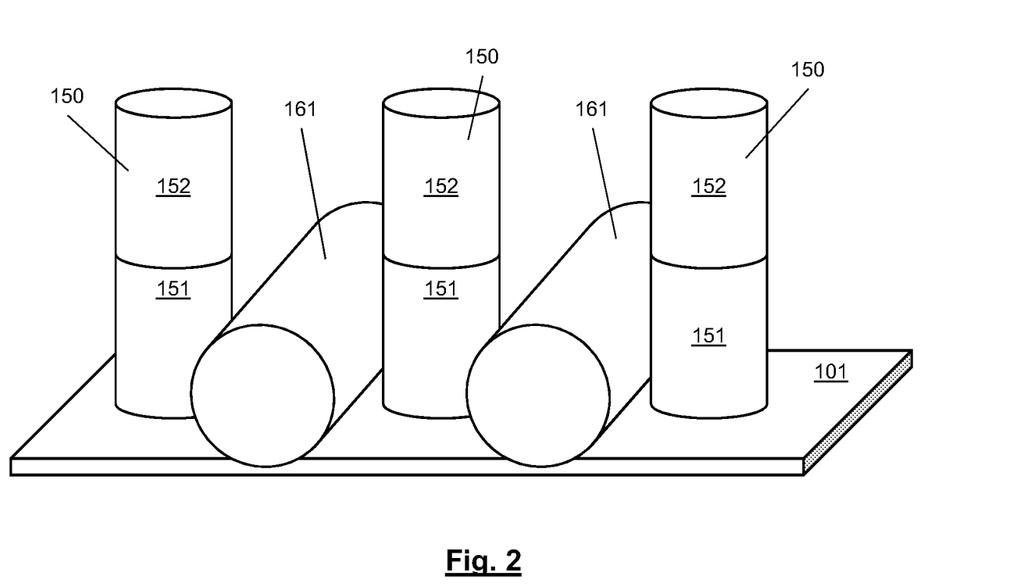

FIG. 2 schematically shows the layer 101 brought into contact with fibres 161 of a layer of the layered structure. The layers are preferably pushed onto each other, such that the surface protrusions 150 of the tab layer 101 enter into spaces between the fibres 161. In cases where the surface protrusions 150 are hooks, they may already (preliminary) engage the fibres 161 of the layered structure.

Figure 3:
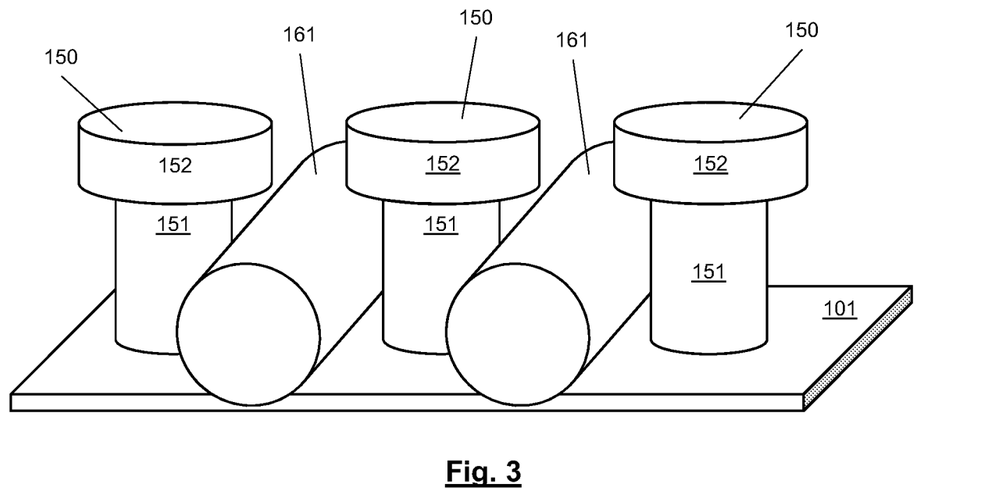

FIG. 3 schematically shows the head portions 152 widened after a deformation step in such a way that the surface protrusions 150 engage the fibres 161 and (at least) a mechanical bond is formed. The deformed head portions 152 may take the form of rivets or in general be wider than the base portions 151, such that the fibres 161 of the layer are engaged by the surface protrusions 150 of the attached portion. Depending on the material and structure of the at least one layer of the layered structure of which the fibres 161 form part, in particular the melting temperatures, some of the head portions 152 may be heat-bonded to or fused with the fibres and creating a permanent engagement Depending on manufacturing process parameters, e.g., time and heat exposure, at least some of the base portions 151 of the surface protrusions 150 of the attached portion may also be at least partly deformed.

The predetermined material of the attached portion 101 with the surface protrusions 150 and the material of the layer comprising the fibres 161 may both be thermoplastic materials. In embodiments, these materials may be different thermoplastic materials with different melting temperatures, the predetermined material of the surface protrusions 150 then preferably having a lower melting temperature.

The predetermined material of the attached portion 101 with the surface protrusions 150 and the material of the layer comprising the fibres 161 may be incompatible polymer blends, also known as immiscible or heterogeneous.

The predetermined material of the attached portion 101 with the surface protrusions 150 and the material of the layer comprising the fibres 161 may be compatible polymer blends.

A first embodiment of the disclosure is described with reference to FIGS. 4-7.

The elongate tab 200 may for example be a disposal tab, here a stretchable or elastic tab attached to an outer layer 210 of the layered structure and provided for being wrapped around the absorbent article. Disposal tabs are typically attached to the backsheet of the diaper, for example in the middle of the rear body portion and oriented in longitudinal direction of the diaper, but it is evident that the disposal tab may be attached elsewhere on the article.

Figure 4:
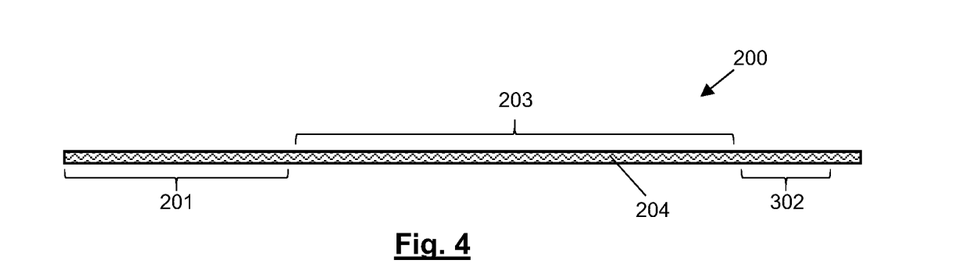
FIGS. 4-7 show a first exemplary embodiment of an elongate tab and a layer of a layered structure and how they are attached to each other according to the present disclosure.

FIG. 4 shows the elongate tab 200 in an initial step of the manufacturing process. The tab may be formed by a single layer 204 of nonwoven. Three zones are defined on the tab: a first zone or portion 201 at one end for first forming surface protrusions and subsequently further deforming the surface protrusions for attachment to the layer 210, a second zone or portion 202 for forming hooks of a fastening portion 206 and a third zone 203 in between which forms a stretch zone in the end product, whereby the tab 200 is stretchable or elastic. If more material is needed to create the surface protrusions, the single layer 204 could be folded in the zones 201, 202 to create multiple layers of material.

Figure 5:
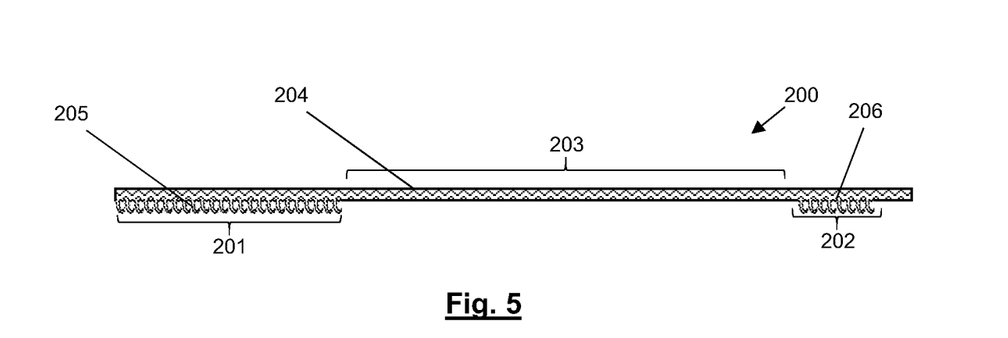

FIG. 5 shows the elongate tab 200 after the formation of surface protrusions in zones 201 and 202, by deformation of the material of the layer 204 using the energy source, e.g., ultrasonic vibrations. In the embodiment shown, the same kind of surface protrusions, in particular hooks 205 and 206 are formed in both zones 201, 202, now "hooked portions", however this is not essential. The formation of hooks 205 in zone 201 has the advantage of already obtaining a preliminary attachment in the subsequent step, but also non-engaging surface protrusions are possible as described elsewhere herein. Hooked portion 201 is shown to be larger than hooked portion 202, but this is not essential. An advantage of a larger hooked portion 201 is a larger zone for the attachment of the tab 200 to the layer 210, whereas hooked portion 202 is to be used for a releasable attachment, i.e., a releasable fastening portion of a hook-and-loop type fastener. The hooks 205 and 206 may be economically formed simultaneously in the same process step as will be explained further below.

Figure 6:
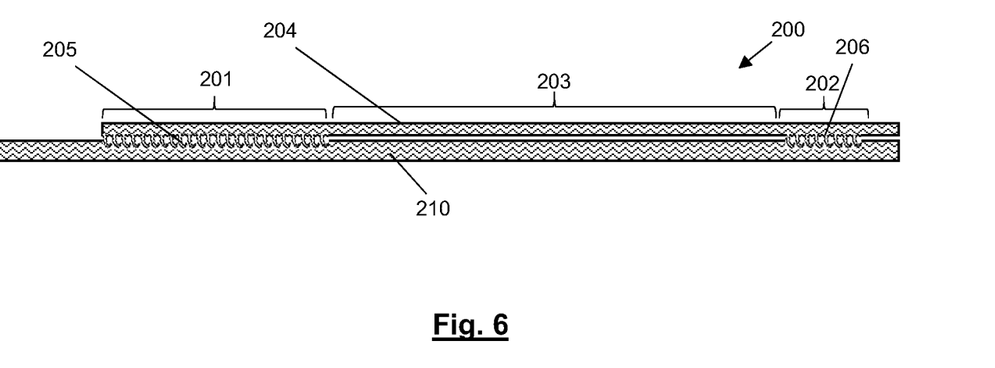

FIG. 6 shows the elongate tab 200 positioned on top of the layer 210 of the layered structure, e.g., the backsheet of a diaper. Both hooked portions 201, 202 engage fibrous loops of the layer 210.

Figure 7:
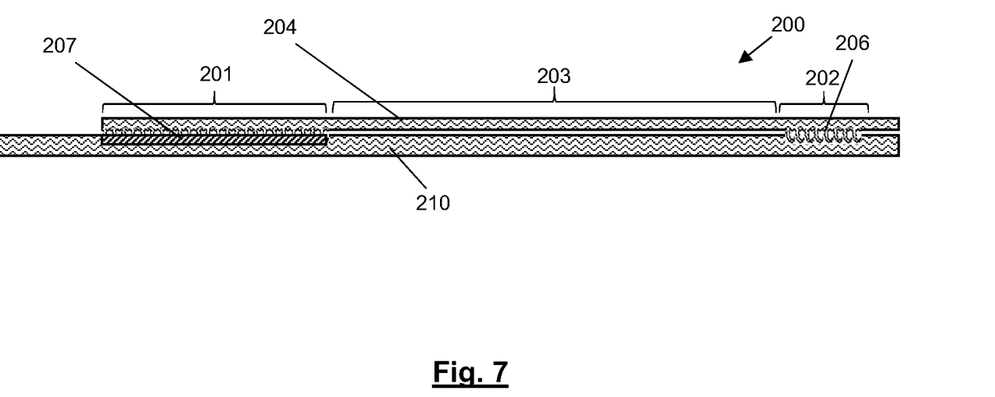

FIG. 7 shows the elongate tab 200 attached to the layer 210 by further deformation of at least some of the hooks 205 in the first zone 201, indicated by deformed portion 207. This further deformation may be performed using the same energy source as used for forming the hooks 205, 206, however also another energy source may be used, preferably chosen from: heat, ultrasonic vibrations, micro waves, infrared radiation. In embodiments, the energy source or parameters thereof may be adapted to also deform part of the material of the layer 210, so as to obtain bonding or fusion of the materials.

The steps described with reference to FIGS. 4-7 may be performed on the layer 210 before, during or after the assembly of the layered structure. The layer 210 may be a layer of the layered structure or a layer which is in turn attached to the layered structure. The layer 210 may for example be a backsheet of a layered structure, a side panel which is attached to a layered structure, or a belt which is attached to a layered structure.

A second embodiment of the disclosure is described with reference to FIGS. 8-10, wherein the elongate tab 300 is a Z-folded disposal tab, attached to an outer layer 310 of the layered structure and provided for being wrapped around the absorbent article. A disposal tab is typically between 60 and 72 mm long in a Z-fold configuration. When unfolded the total length of the disposal tab may be about 100 to 200 mm. The width of a disposal tape is typically between 10 and 20 mm. Disposal tabs are typically attached to the backsheet of the diaper, for example in the middle of the rear body portion and oriented in longitudinal direction of the diaper, but it is evident that the disposal tab may be attached elsewhere on the article.

Figure 8:
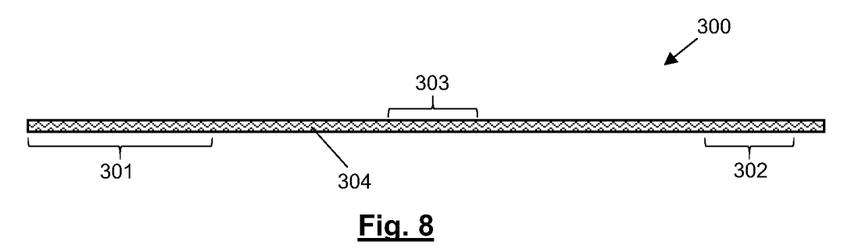
FIGS. 8-10 show a second exemplary embodiment of an elongate tab and a layer of a layered structure and how they are attached to each other according to the present disclosure.

FIG. 8 shows the tab 300 in an initial state. The tab may be formed by a single layer 304 of nonwoven. Three zones are defined on the tab: a first zone or portion 301 at one end for first forming surface protrusions 305 and subsequently further deforming the surface protrusions for attachment to the layer 310, a second zone or portion 302 for forming hooks of a fastening portion 306 and a third zone 303 on the opposite side of the tab for forming further hooks 307.

Figure 9:
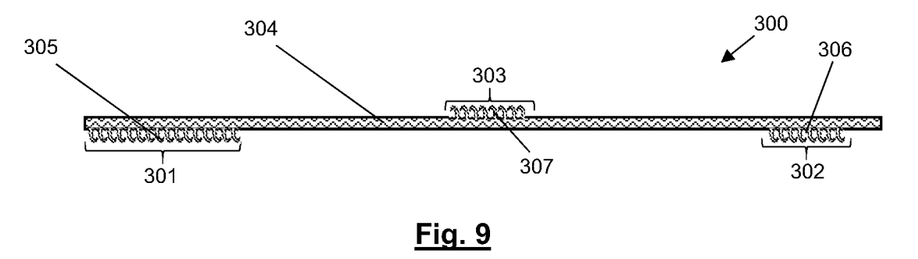

FIG. 9 shows the elongate tab 300 after the formation of surface protrusions in zones 301, 302 and 302, by deformation of the material of the layer 304 using the energy source, e.g., ultrasonic vibrations. In the embodiment shown, the same kind of surface protrusions, in particular hooks 305, 306 and 207 are formed in all zones 301, 302, 303, now "hooked portions", however this is not essential. The formation of hooks 305 in zone 301 has the advantage of already obtaining a preliminary attachment in the subsequent step, but also non-engaging surface protrusions are possible as described elsewhere herein. Hooked portion 301 is shown to be larger than hooked portions 302, 303, but this is not essential. An advantage of a larger hooked portion 301 is a larger zone for the attachment of the tab 300 to the layer 310, whereas hooked portions 302, 303 are to be used for a releasable attachment. The hooks 305, 306, 307 may be economically formed simultaneously in the same process step as will be explained further below.

Figure 10:
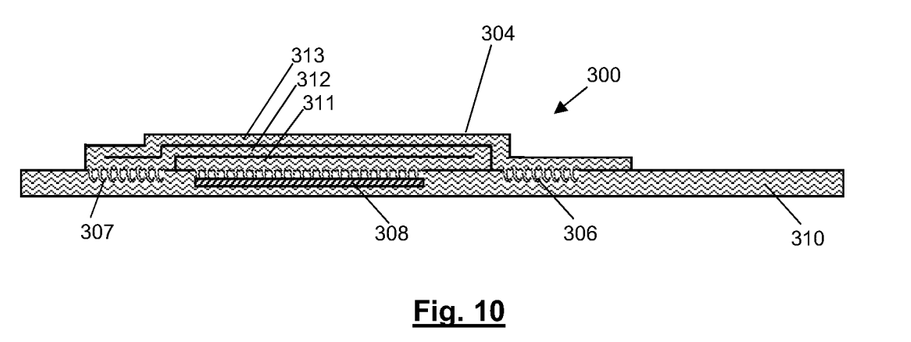

FIG. 10 shows the tab 300 after attachment to the layer 310 and after being Z-folded. A bottom layer 311 of the Z-folded tab 300 comprises the attached portion which is attached to the outer layer 310 by means of the further deformed surface protrusions, indicated by deformed portion 308. A middle layer 312 lies on top of the bottom layer and comprises hooked portion 307 which extends beyond the bottom layer and is releasably fastened to the outer layer 310 of the absorbent article. A top layer 313 lies on top of the middle layer and comprises the hooked portion 306 which extends beyond the bottom and middle layers and is releasably fastened to the outer layer 310 of the absorbent article.

In use, when a user wants to dispose of the article, the user pulls the tab 300 at the end with the hooked portion 306 to release its hooks from the outer layer 310 and unfolds the tab, thereby also releasing the hooks 307 from the outer layer 310. The unfolded tab can subsequently be wrapped around the article and the hooked portion 306 as fastening portion for subsequently fastening to a different region or landing zone on the article.

In alternative embodiments, the layers of a Z-folded disposal tab may be adherent to each other, for example by means of adhesive between the bottom and middle layer and between the middle and top layer, or as a result of the material of the layers being self-adherent.

The steps described with reference to FIGS. 8-10 may be performed on the layer 310 before, during or after the assembly of the layered structure. The layer 310 may be a layer of the layered structure or a layer which is in turn attached to the layered structure. The layer 310 may for example be a backsheet of a layered structure, a side panel which is attached to a layered structure, or a belt which is attached to a layered structure.

Figure 11:
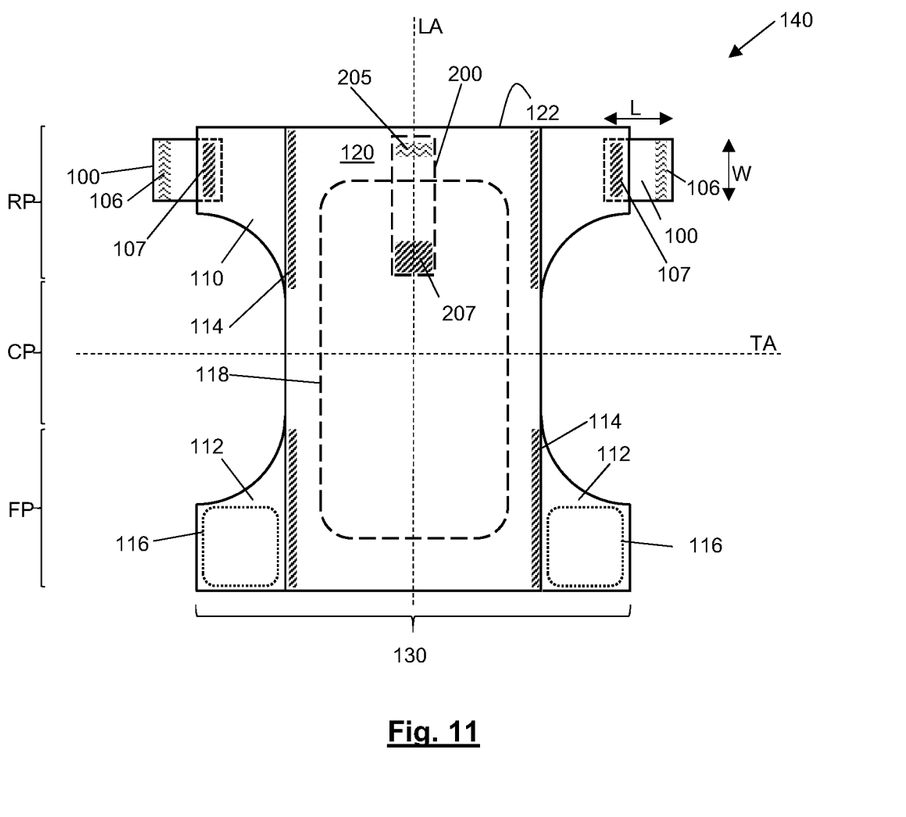
FIG. 11 shows a top view of an exemplary absorbent article according to the present disclosure.

FIG. 11 schematically shows a top view onto an embodiment of an absorbent article, such as a diaper according to the disclosure. The diaper 140 is unfolded and in a flat state. The diaper comprises a layered structure 130 which is composed of a central part with a (permeable) topsheet 120 and a (impermeable) backsheet 122 on opposite sides of a core 118 of absorbent material. In other words, the diaper 140 comprises an absorbent core 118 sandwiched between a liquid-permeable topsheet 120 and a liquid-impermeable backsheet 122. The diaper 140 may comprise one or more elongate tabs attached to the layered structure 130, such as for example fastening tabs 100 for fastening a diaper around the wearer's waist and/or a disposal tab 200 to be used upon disposal of the article. Both these types of tabs 100, 200 are shown in FIG. 11, but the disclosure also extends to absorbent articles comprising only one such type of tab or another type of elongated tab attached to its layered structure.

The diaper being arranged along a longitudinal axis "LA" and a transversal axis "TA" extending in a perpendicular direction in relation to the longitudinal axis, said article comprising a front portion "FP", a back or rear portion "RP" and a crotch portion "CP" extending between the front portion and the back portion. The diaper has a longitudinal center line extending along the longitudinal axis. The front portion and the back portion each have a waist edge. The front portion is intended to be oriented in a direction towards the wearers belly during use of the article.

Preferably, the absorbent core 118 is disposed at least in the crotch portion "CP". The absorbent core is possibly extending in the front portion "FP" and in the rear portion "RP". The topsheet 120 is arranged at the surface of the diaper, i.e., at the side which is facing the wearer, whereas the backsheet 122 is arranged at the underside of the article. The absorbent structure, i.e., the core 118 is for absorbing body excudates from a wearer to provide a dry and comfortable fit for the wearer.

Various types of materials may be used for the absorbent article. The topsheet is arranged to face the wearer of the absorbent article when worn. The topsheet may be formed by a fluid permeable nonwoven fabric or film which is made of thermoplastic synthetic fibers. The topsheet may be sufficiently liquid-permeable to allow discharged body fluids to penetrate through the thickness of the topsheet. Also, the topsheet may be suitably manufactured from a material which is compliant and soft-feeling to the skin of the wearer. The topsheet may consist of a single layer or have a laminate structure comprising a plurality of layers, for example, two or more layers. The layers may be made of the same material, or some or all the layers may be made of different materials.

The layer of the topsheet 120 or, for the case of a laminate structure, one, some, or all layers of the topsheet may be made of a single material or have plural portions made of different materials, e.g., within different parts of the wearer-facing surface of the topsheet.

The layer of the topsheet or, for the case of a laminate structure, one, some or all layers of the topsheet may be a nonwoven material, a perforated plastic film, a plastic or textile mesh, or a liquid permeable foam layer.

The layer of the topsheet or, for the case of a laminate structure, one, some or all of the layers of the topsheet may be, for example, a hydrophilic, non-apertured nonwoven web of fibers, such as natural fibers, e.g., cotton or pulp fibers, synthetic fibers, e.g., polyester or polypropylene fibers, or a combination of these fibers.

The topsheet may have a basis weight in the range of 8-40 g/m2. However, the disclosure is not limited to topsheets having this basis weight only.

The backsheet 122 may be constituted by a liquid-impermeable and breathable layer such as a polymeric film, for example a film of polyethylene or polypropylene. According to different embodiments, the materials which may be used for the backsheet include thin and flexible fluid impermeable plastic films, or fluid impermeable nonwoven materials, fluid impermeable foams and fluid impermeable laminates.

The backsheet may be formed by a single layer, but may alternatively be formed by a multi-layered structure, i.e., a laminate, wherein at least one layer is fluid impermeable. Furthermore, the backsheet 122 may be elastic in any direction.

Furthermore, the backsheet may have a laminate structure comprising a liquid barrier sheet and a nonwoven layer arranged on top of each other (not shown in detail in the drawings), wherein the nonwoven layer is arranged at an outer side away from the wearer of the absorbent article when worn.

The nonwoven layer may be made of thermoplastic polymer material fibers or filaments. The nonwoven layer may be formed by a variety of different processes, such as spunbonding, airlaying, meltblowing or bonded carded web formation processes. The nonwoven layer may be made of an SMS (spunbond/meltblown/spunbond) or SS (spunbond/spunbond) nonwoven material of polypropylene or bicomponent fibers of polypropylene and polyethylene, or of a combination of such materials.

The liquid barrier sheet may be made of a plastic material, for example a thermoplastic film material, and/or a nonwoven material. For example, the liquid barrier sheet may be formed as a plastic layer, e.g., a thermoplastic layer, or a plastic film, e.g., a thermoplastic film. Forming the liquid barrier sheet of a plastic material, such as a thermoplastic film material, allows for a particularly good printability of the liquid barrier sheet. The liquid barrier sheet may also contain paper fibers.

The liquid barrier sheet may be a liquid impermeable, breathable or non-breathable layer. The liquid barrier sheet may consist of a single layer or have a laminate structure with a plurality of layers, e.g., two or more layers, three or more layers, or four or more layers. The layers of the liquid barrier sheet may be laminated, bonded or attached to each other, for example, by thermo and/or mechanical bonding, such as thermo-sealing, ultrasonic bonding, such as ultrasonic welding, an adhesive or adhesives, stitching or the like.

The liquid barrier sheet may be a breathable microporous film. The microporous film may be made of a material comprising at least two basic components, namely a thermoplastic elastomeric polyolefin polymer and a filler. These components and, in some embodiments, additional other components may be mixed together, heated and subsequently extruded into a mono-layer or multi-layer film using any one of various film-producing processes, such as cast embossed, chill and flat cast, and blown film processes.

Furthermore, the absorbent core 118 provided between the topsheet and the backsheet to absorb the liquid, such as urine or other bodily fluids, which has passed through the topsheet. The absorbent core may be made of one layer only, made from any suitable absorbent or liquid uptake material, such as one or more layers of cellulose fluff pulp, foam, fiber waddings or the like.

The absorbent core may comprise suitable amounts of superabsorbent particles. Such superabsorbent material is well known in the field of absorbent articles, and is constituted by a water-swellable and water-insoluble material which is capable of absorbing large quantities of fluid upon formation of a hydrogel. The absorbent core may contain superabsorbent material in the form of fibers or particles of absorbent polymer material. For example, the superabsorbent material may be surface cross-linked, partially neutralized polyacrylates. Furthermore, a core cover may surround the core and may be made of nonwoven material, with a basis weight of 5-20 g/m2.

The superabsorbent material, e.g., the superabsorbent fibers or particles, may be mixed with other absorbent or liquid uptake material or materials, such as cellulose fluff pulp, and/or arranged in pockets or layers in the absorbent core.

The absorbent core may further comprise components for improving the properties of the absorbent core. For example, the absorbent core may comprise a binder or binders, such as binder fibers.

Furthermore, as known by the skilled person, the various layers of the absorbent article may be attached by means of adhesive material.

One or more additional layers may be provided in the absorbent article. For example, an acquisition layer may be arranged between the absorbent core and the topsheet. Such an additional layer may for example be in the form of an airlaid layer, a spunlace layer, a high-loft, foam or any other type of material layer which may be used in an absorbent article to act as a liquid acquisition and absorption layer. The acquisition layer is adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibres are dispersed into a fast-moving air stream and condensed onto a moving screen by means of pressure and vacuum.

In the embodiment of FIG. 11, first and second side panels 110, 112 are attached to the longitudinal edges of the central part by means of welds 114 and in this way form part of the layered structure 130. The first side panels 110 are located at the rear body portion RP of the diaper and provided with fastening tabs 100, which may be attached to the back side of the panels 110 (i.e., the outside of the diaper 140), but the fastening tabs 100 could also be attached to the front side or a different layer. The second side panels 112 are located at the front body portion FP of the diaper. The back sides of the second side panels 112, i.e., the outer side, which is facing away from the user during use, provide landing zones 116 for the fastening portions 106 of the fastening tabs 100. In FIG. 11, the tabs 100 are shown in released position, i.e., released and unfolded by the user before use. In packaged condition, i.e., as the article is sold, the tabs 100 are normally in folded position. Instead of the separate side panels, both the topsheet and the backsheet may extend laterally outside the absorbent core along the perimeter of the absorbent article and form the side panels.

The fastening tabs 100 typically have a length L between 40 and 75 mm and a width W between 20 and 50 mm. Each tab 100 comprises a layer of the predetermined material described herein, deformable by means of an energy source, in particular ultrasonic vibrations. A first portion 107 is used for attachment to a layer of the layered structure 130, in particular a side panel 110, and is a portion with deformed surface protrusions as described elsewhere herein. A second portion 106 comprises hooks and is usable as a fastening portion 106 of a hook-and-loop type fastener together with the landing zone 116.

The disposal tab 200 shown in FIG. 11 is a disposal tab according to FIGS. 4-7, attached to the backsheet 122 of the diaper 140. Alternatively, the diaper may also have a disposal tab 300 according to FIGS. 8-10, or another disposal type according to the present disclosure.

In alternative embodiments, the elongate tab may be a belt attached to the absorbent article, for example to a backsheet, and provided for holding the article around the wearer's waist, i.e., the article then being for example a belt diaper. A belt diaper having a belt may have two belt portions i.e., two belts extending on either side of the rear end or the front end of the chassis or the absorbent part. When putting on a belt diaper the two belt portions, i.e., the two belts are intended to be fastened around the waist of the wearer in a first stage. The front end or the rear end of the absorbent part of the belt diaper is hanging loose from the belt between the legs of the wearer. Once the belt portions have been joined together, the absorbent part is led between the user's legs and fastened to the belt, wherein the belt comprises fixing surfaces intended to stick to a fixing element arranged on the absorbent part of the diaper by its free transverse edge For such an absorbent article, which comprises two belt portions only one of the belt portions may comprise a fastening portion to fasten the belts together when they overlap during use. Alternatively, both belts may have fastening portions in opposite directions, so that the fastening portion on the first belt attach the second belt and the fastening portion of the second belt attach the first belt when they are overlapping each other during use.

In embodiments according to the disclosure, the at least one elongate tab, e.g., fastening tabs 100 or disposal tabs 200, 300 as described above, may be stretchable or elastic. For example, the disposal tab 200 may be elastic or stretchable to an extent that it is capable of being wrapped around the absorbent article, for example stretchable by 50 to 300%.

Figure 12:
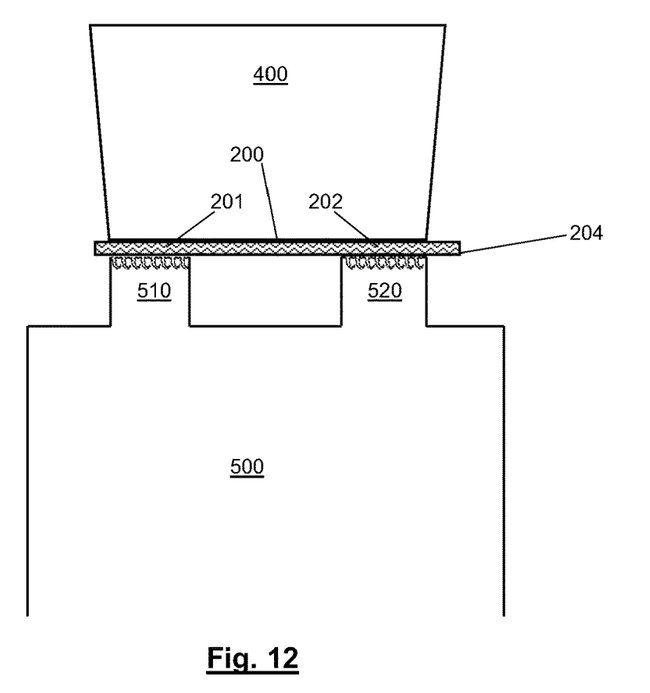
FIGS. 12 and 13 show exemplary embodiments of manufacturing steps according to the present disclosure.
Figure 13:
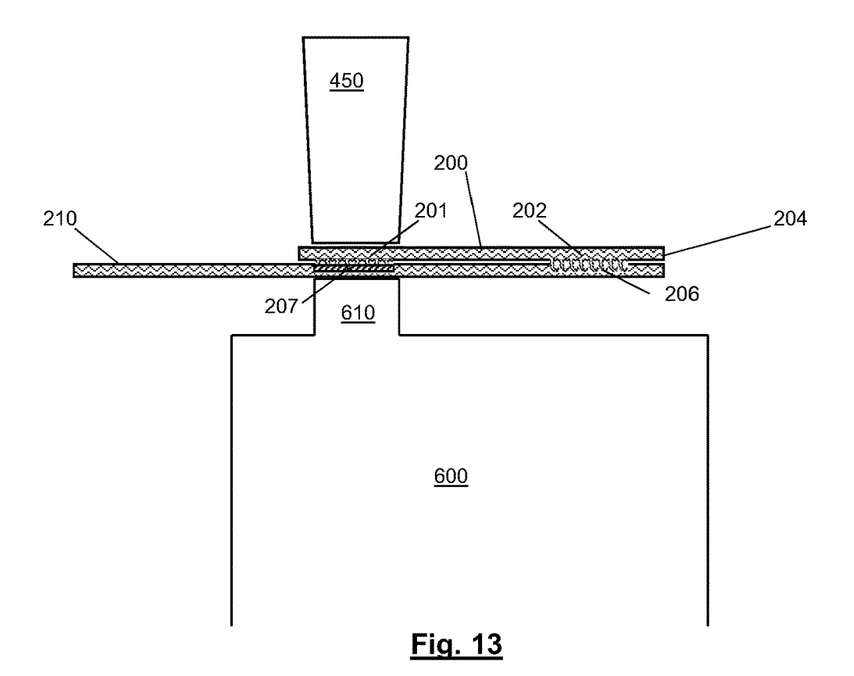

FIGS. 12 and 13 show an embodiment of successive steps of the method of manufacturing the absorbent articles described herein, in particular, the steps of forming surface protrusions in the first and second portions 201, 202 of an elongate tab 200 and, subsequently, positioning the elongate tab 200 on the layer 210 of the layered structure and attaching it thereto by deforming the surface protrusions of the first portion 201 of the elongate tab. These steps may be performed by deforming the predetermined material by means of the same energy source. In FIGS. 12 and 13, a tab according to FIGS. 4-7 is shown, but the steps can also be applied on the other elongate tabs described herein.

In the embodiments of FIGS. 12 and 13, ultrasonic vibrations are used as energy source. The process for forming surface protrusions using ultrasonic energy is known from WO 2010/085492 A1 and U.S. Pat. No. 6,746,434 B2. Here, this process is simultaneously used for forming surface protrusions in both zones 201, 202. To this end, the tab 200 is positioned between an anvil 500 and an ultrasonic horn 400. The anvil 500 (shown in cross-section in FIG. 12) may be a rotating anvil which has annular protruding parts 510, 520.

In the step of FIG. 12, the annular protrusions 510, 520 have recesses in their top sides which are shaped for forming the hooked portions 205, 206. The tab layer 204 is positioned between the annular protrusion 510 of the anvil and the ultrasonic horn 400, such that the first portion 201 and the second portion 202 are deformed by the ultrasonic energy into the hooked portions with hooks 205, 206. If more material is needed to create the surface protrusions, the single layer 204 could be folded in the zones 201, 202 to create multiple layers of material.

In the step of FIG. 13, the tab 200 is positioned on the layer 210. The correct position may for example be verified by means of a vision system. The tab 200 and 210, in particular the zone 201 with surface protrusions 205, are brought between a second anvil 600 and ultrasonic horn 450. The second anvil 600 may have an annular protrusion 610 and the horn 450 may be sized to apply energy above this protrusion 610 only. By the ultrasonic vibrations, at least some of the surface protrusions 205, in particular the head portions thereof (see FIGS. 1-3), are further deformed, possibly together with material of the layer 210, to mechanically bond the tab 200 to the layer 210, as indicated by deformed zone 207.

As an alternative to FIG. 12, the ultrasonic horn 400 could have recesses, for example to form hooks in the other direction (i.e., on the top side of the tab in the orientation shown in FIG. 12) or in two different directions (i.e., on both sides of the tab).

Figure 14:
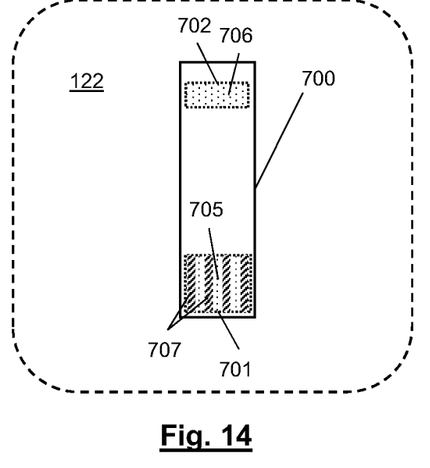
FIG. 14 shows a top view of a portion of another exemplary embodiment of an absorbent article according to the present disclosure.

FIG. 14 shows a top view of a portion of another embodiment of an absorbent article according to the present disclosure. The figure shows a portion of the backsheet 122 of the layered structure article and an elongate tab 700 attached thereto. The elongate tab, e.g., a disposal tab, comprises at least portions 701, 702 in the predetermined material described herein, deformable by means of the energy source. The tab may further have any other characteristics as described herein. The backsheet 122 is for example a nonwoven. The first portion 701 comprises surface protrusions 705, integrally formed of said material. The surface protrusions 705 may have any form as described elsewhere herein. In a number of sub-regions of the first portion 701, at least head portions of the surface protrusions 705 have been further deformed, e.g., to form ultrasonic welds 707, by which the first portion 701 of the tab is attached to the backsheet 702. The second portion 702 comprises hooks 706 and is a fastening portion which is releasably fastened to the backsheet 122 and can be pulled loose by a user, e.g., to wrap the tab around the article and fasten the portion 702 to a different part of the backsheet for disposal of the article. In the embodiment of FIG. 14 the materials of the tab (portions) and the backsheet may be incompatible polymers.

The invention claimed is:

1. An absorbent article comprising:
   a layered structure with an absorbent material sandwiched between at least two layers of said layered structure and at least one elongate tab, each of the at least one elongate tab comprising: an attached portion by which the tab is attached to at least a first layer of the layered structure, a fastening portion configured for releasably engaging a landing zone on the absorbent article, and a stretchable portion in between the attached portion and the fastening portion,
   wherein each of the at least one elongate tab is a film, a nonwoven web, a sheet or a laminate which comprises a complete layer made of a predetermined material which is deformable by an energy source,
   wherein each of the at least one elongate tab is stretchable by 50% to 300%,
   wherein the attached portion comprises a plurality of surface protrusions which are integrally formed of said predetermined material, each of said surface protrusions comprising a base portion and a head portion above the base portion, and
   wherein the attached portion is attached to said first layer of the layered structure by deformed head portions of at least some of said surface protrusions.

2. The absorbent article according to claim 1, wherein the deformed head portions are wider than the base portions of the surface protrusions, such that fibres of at least said first layer are engaged by the surface protrusions of the attached portion.

3. The absorbent article according to claim 1, wherein the deformed head portions are bonded to or fused with material of at least said first layer.

4. The absorbent article according to claim 1, wherein the fastening portion comprises hooks which are integrally formed of said predetermined material.

5. The absorbent article according to claim 1, wherein the at least one elongate tab is fully made of said predetermined material.

6. The absorbent article according to claim 1, wherein said predetermined material is a thermoplastic material deformable by an energy source chosen from: heat, ultrasonic vibrations, micro waves, infrared radiation.

7. The absorbent article according to claim 6, wherein said first layer is made of a different thermoplastic material having a different melting temperature than that of said predetermined material.

8. The absorbent article according to claim 1, wherein the predetermined material of the plurality of surface protrusions of the attached portion and a material of the first layer to which the tab is attached are incompatible polymer blends.

9. The absorbent article according to claim 1, wherein the at least one elongate tab is permanently attached to at least the first layer of the layered structure.

10. The absorbent article according to claim 1, wherein said at least one elongate tab is a disposal tab attached to an outer layer of the layered structure and configured for being wrapped around the article.

11. The absorbent article according to claim 10, wherein the disposal tab is a Z-folded tab, a bottom layer of the Z-folded tab comprising the attached portion and a top layer of the Z-folded tab comprising the fastening portion.

12. The absorbent article according to claim 11, wherein layers of the Z-folded tab adhere to each other, the layers including at least the bottom and top layers of the Z-folded tab.

13. The absorbent article according to claim 10, wherein the disposal tab is stretchable or elastic such that the disposal tab is configured for being wrapped around the article.

14. The absorbent article according to claim 1, wherein the at least one elongate tab is a fastening tab attached to a first side portion of the layered structure and configured for being fastened to one or more landing zones on a surface of the layered structure.

15. A method of manufacturing an absorbent article with an absorbent material sandwiched between at least two layers of said layered structure and at least one elongate tab, the method comprising the steps of:
- a) providing a first layer of said layered structure and the at least one elongate tab, wherein each of the at least one elongate tab is a film, a nonwoven web, a sheet or a laminate which comprises a complete layer made of a predetermined material which is deformable by an energy source and comprises a first portion, a second portion and a stretchable portion in between said first and second portions, wherein each of the at least one elongate tab is stretchable by 50% to 300%;
- b) forming surface protrusions on at least said first portion of each of the at least one elongate tab by deforming said predetermined material by said energy source;
- c) positioning each of said at least one elongate tab with respect to said first layer, such that the first portion of the tab overlaps with the first layer and said surface protrusions are directed to the first layer; and
- d) attaching the first portion of each of said at least one elongate tab to said first layer by further deforming head portions of at least some of said surface protrusions of the first portion by said energy source, thereby creating an attached portion wherein the tab is attached to said layer by said deformed head portions.

16. The method according to claim 15, wherein the deformed head portions are wider than base portions of the surface protrusions, such that fibres of said first layer are engaged by the surface protrusions of the attached portion.

17. The method according to claim 15, wherein the deformed head portions are bonded to or fused with material of said first layer.

18. The method according to claim 15, wherein a second portion of each tab is also made of said predetermined material and surface protrusions are also be formed on said second portion in step b), thereby creating in said second portion a fastening portion provided for releasably engaging a landing zone on the absorbent article.

19. The method according to claim 15, wherein the at least one elongate tab is fully made of said predetermined material.

20. The method according to claim 15, wherein said predetermined material is a thermoplastic material and wherein the energy source is chosen from: heat, ultrasonic vibrations, micro waves, infrared radiation.

21. The method according to claim 20, wherein said layer is made of a different thermoplastic material having a different melting temperature than that of said predetermined material.

22. The method according to claim 15, wherein the attached portion includes the predetermined material, and the predetermined material of the attached portion and a material of the layer to which the tab is attached are incompatible polymer blends.

23. The method according to claim 22, wherein said thermoplastic material of said layer to which the tab is attached is also deformed by said energy source.

24. The method according to claim 15, further comprising a step of folding said at least one elongate tab.

* * * * *